(12) United States Patent
Cauceglia (10) Patent No.: US 12,064,758 B2
(45) Date of Patent: Aug. 20, 2024

(54) STABILIZED REAGENT COMPOSITIONS, SYSTEMS AND METHODS USING THE SAME

(71) Applicant: Watts Regulator Co., North Andover, MA (US)

(72) Inventor: Dorian Cauceglia, Fort Myers, FL (US)

(73) Assignee: WATTS REGULATOR CO., North Andover, MA (US)

( * ) Notice: Subject to any disclaimer, the term of this patent is extended or adjusted under 35 U.S.C. 154(b) by 256 days.

(21) Appl. No.: 17/407,306

(22) Filed: Aug. 20, 2021

(65) Prior Publication Data
US 2023/0058190 A1    Feb. 23, 2023

(51) Int. Cl.
*B01L 3/00* (2006.01)
*B01D 15/36* (2006.01)
(Continued)

(52) U.S. Cl.
CPC ............ *B01L 3/502* (2013.01); *B01D 15/363* (2013.01); *B01L 3/523* (2013.01); *B01L 3/567* (2013.01);
(Continued)

(58) Field of Classification Search
CPC .......... B01L 2200/16; B01L 2300/069; B01L 2400/0605; B01L 2300/12; G01N 2021/7763
See application file for complete search history.

(56) References Cited

U.S. PATENT DOCUMENTS 3,647,397 A    3/1972  Coleman
5,259,537 A   11/1993  Beers et al.
(Continued)

FOREIGN PATENT DOCUMENTS

CN     102279177 A    12/2011
CN     102937579 B     8/2014
(Continued)

OTHER PUBLICATIONS

Purolite A300 Polystyrenic Gel, Type II Strong Base Anion Resin, Chloride form, FDA 21 CFR 173.25, King of Prussia, PA, Jun. 11, 2021, pp. 1-3.
(Continued)

*Primary Examiner* — Maris R Kessel
*Assistant Examiner* — Alea N. Martin
(74) *Attorney, Agent, or Firm* — Grossman, Tucker, Perreault & Pfleger, PLLC (57) ABSTRACT

Stabilized indicator compositions, and systems and methods using the same are described. In embodiments the stabilized indicator compositions include a solvent, an indicator, a stabilizer for the indicator, and optionally a buffer. In embodiments the indicator is or includes N, N-diethyl-p-phenylene diamine (DPD). Systems and methods utilizing the stabilized indicator composition to determine an amount of at least one constituent in a test sample (e.g., water) are also described. In embodiments, the systems and methods remove the stabilizer from the stabilized indicator composition to produce a fluid flow containing un stabilized indicator, which is then combined with a fluid from a sample source to form a test sample for analysis.

13 Claims, 7 Drawing Sheets

(51) Int. Cl.
*G01N 21/78* (2006.01)
*G01N 33/18* (2006.01)

(52) U.S. Cl.
CPC .............. *G01N 21/78* (2013.01); *G01N 33/18* (2013.01); *B01L 2200/16* (2013.01); *B01L 2300/069* (2013.01); *B01L 2300/12* (2013.01); *B01L 2400/0605* (2013.01)

(56) References Cited

U.S. PATENT DOCUMENTS

| | | | |
|---|---|---|---|
| 6,328,896 B1 * | 12/2001 | Atnoor | C02F 1/42 210/900 |
| 6,749,091 B2 | 6/2004 | Connelly et al. | |
| 7,794,660 B2 | 9/2010 | Connelly et al. | |
| 8,993,337 B2 | 3/2015 | Evtodienko et al. | |
| 9,545,781 B2 | 1/2017 | Ismail et al. | |
| 10,287,180 B1 | 5/2019 | Kurani et al. | |
| 2007/0178010 A1 | 8/2007 | Connelly et al. | |
| 2011/0014687 A1 | 1/2011 | Nakamura et al. | |
| 2011/0162964 A1 * | 7/2011 | Freydina | C02F 1/66 204/632 |
| 2020/0332236 A1 | 10/2020 | Meadows et al. | |
| 2020/0399569 A1 | 12/2020 | Meadows et al. | |

FOREIGN PATENT DOCUMENTS

| | | |
|---|---|---|
| CN | 105372194 A | 3/2016 |
| CN | 109406425 A | 3/2019 |
| CN | 109612951 A | 4/2019 |
| JP | 2003215119 A | 7/2003 |
| WO | 2011100789 A1 | 8/2011 |
| WO | 2017044532 A1 | 3/2017 |
| WO | 2020180285 A1 | 9/2020 |
| WO | 2020185844 A1 | 9/2020 |

OTHER PUBLICATIONS

Harp, "Current Technology of Chlorine Analysis for Water and Wastewater", Technical Information Series—Booklet No. 17, USA, 2002, pp. 1-30.

Reliable Chlorine Monitoring, HF Scientific, USA, ES-HF-CLX 2020-38, Ft. Meyers, FL, 4 pages.

Owner's Manual CLX OnLine Residual Chlorine Monitor, HF Scientific, Catalog #24420 (Apr. 2018) REV 6.0, Ft. Myers, FL, pp. 1-34.

International Search Report and Written Opinion from corresponding PCT Appln. No. PCT/US22/75059, dated Jan. 26, 2023. 9 pages.

* cited by examiner

STABILIZED REAGENT COMPOSITIONS, SYSTEMS AND METHODS USING THE SAME

TECHNICAL FIELD

The present disclosure relates to stabilized reagent compositions, systems and methods using the same. In particular, the present disclosure relates to stabilized reagent compositions for use in detecting a level of chlorine in a sample, and systems and methods using the same.

BACKGROUND

Fluid content monitors for testing drinking, wastewater, and industrial water supplies for the presence of residual chlorine and other constituents are known. Conventional fluid content monitors that monitor water for residual chlorine utilize colorimetric reagent technology, in which a reagent that includes an indicator such a DPD (N, N-diethyl-p-phenylene diamine) and a buffer (for adjusting pH) is dispensed into a water sample in a cuvette. The indicator causes the color of the water sample to change to differing degrees depending on the concentration of chlorine in the water. The concentration of chlorine is then determined by colorimetric analysis (i.e., colorimetrically) by analyzing the color of the water sample containing the indicator with an appropriate electronic tester.

Colorimetric measurements using DPD as an indicator have been proven to provide a reliable and accurate method of determining the amount of chlorine present in a water sample. Despite its usefulness, however, DPD is not without limitations. For example, DPD (particularly in an aqueous solution) can oxidize over time, which can affect its ability to accurately indicate the concentration of residual chlorine in a sample. Reagents that include an aqueous solution of DPD therefore have a limited shelf life before they must be replaced to ensure that the reagent enables an accurate measurement of chlorine content in a sample. An aqueous solution of DPD typically has a shelf life of about 30 days at 55° C. before it must be replaced due to oxidation. The lifetime of such a solution can be extended by maintaining it at a lower fixed temperature. For example, an aqueous solution of DPD may have a shelf life of about 90 days at a fixed temperature of 25° C. before it must be replaced due to oxidation.

With the foregoing in mind, many fluid content monitors (including the CLX line of fluid content monitors sold by HF Scientific) are configured to use reagents that include an aqueous solution of DPD to facilitate colorimetric determination of the chlorine content of a sample. Due to the tendency of DPD to oxidize (particularly in aqueous solution), the reagents used by such systems must be changed periodically to ensure that the system provides accurate results. Not only is the need to replace the aqueous reagent is inconvenient and time consuming, it is also wasteful as significant amounts of unused reagent may be discarded each time the reagent is replaced.

Accordingly, there is a need in the art for stabilized reagent compositions (particularly for detecting residual chlorine in a sample), and systems and methods using the same. The present disclosure is aimed at that need.

BRIEF DESCRIPTION OF THE DRAWINGS

Features and advantages of various embodiments of the claimed subject matter will become apparent as the following Detailed Description proceeds, and upon reference to the Drawings, wherein like numerals designate like parts, and in which:

DETAILED DESCRIPTION

Figure 1A:
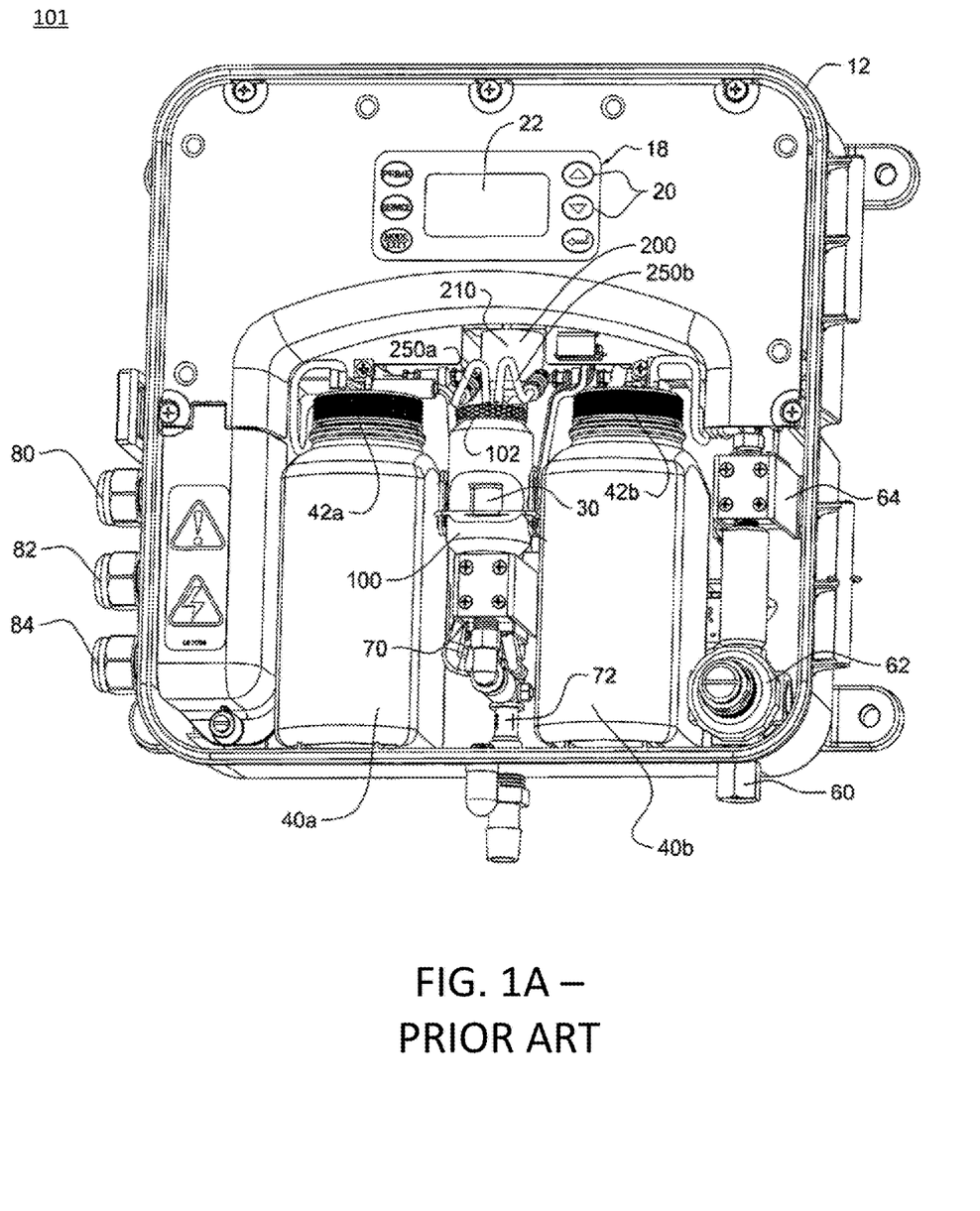
FIG. 1A illustrates one example of a fluid content monitor consistent with the prior art.
Figure 1B:
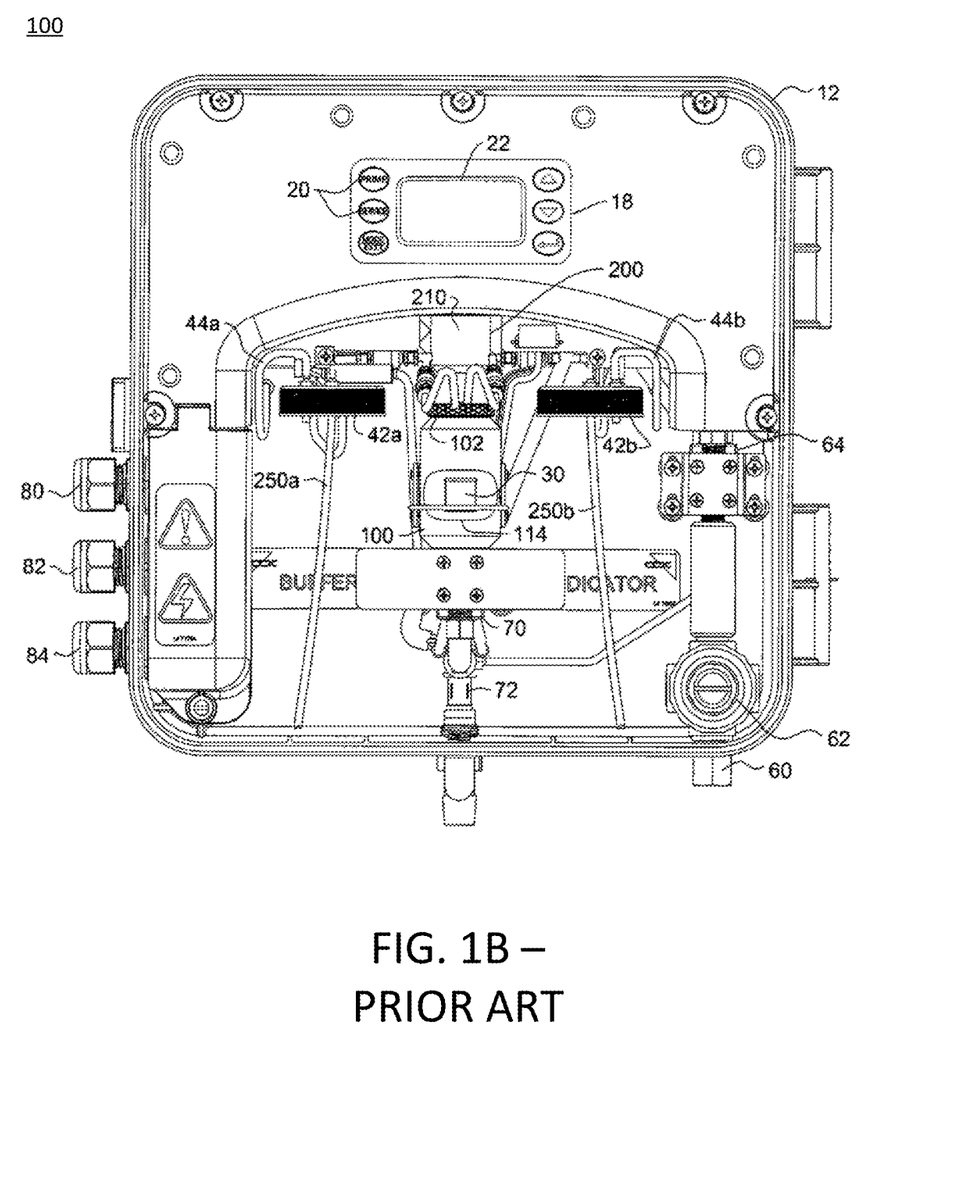
FIG. 1B illustrates the fluid content monitor of FIG. 1A with reagent containers removed.

As noted in the background, on-line fluid content monitoring systems that utilize DPD to detect residual and total chlorine in a water sample are known. FIGS. 1A and 1B depict one example of such a system, and the operation of that system is briefly described herein for the sake of clarity. A full description of the system shown in FIGS. 1A and 1B is provided in U.S. Pat. No. 7,794,660, the entire content of which is incorporated herein by reference.

System 101 is a chlorine monitor that can be used to measure residual free or total chlorine in a water sample. System 101 includes a case 12 with a removable cover (not shown). A control panel 18 with controls 20 and a display 22 is provided to allow operator monitoring and control over the system 101. System 101 further includes a colorimeter 100 that receives a cuvette 30, and a pump assembly 200 including a pump 210 for transferring reagents from reagent containers 40a, 40b to a cuvette 30. Reagent container 40a may contain a buffer. Reagent container 40b contains a solvent (e.g., water) and an (un-stabilized) indicator, such as (un-stabilized) DPD.

System 101 further includes a cuvette portal 114 for removably receiving the cuvette 30. System 101 further includes an inlet line 60 to receive a water sample to be tested, and a pressure regulator 62 and an inlet valve 64 to control flow of the water sample to cuvette 30 for testing. Electrical power is provided to system 101 via a first connector 80. Second and third connectors 82, 84 enable system 101 to connect to an alarm and/or one or more remote locations. Colorimeter 100 is generally configured to determine the concentration of at least one constituent (e.g., chlorine) in a sample within cuvette 30.

System 101 further includes a controller (not shown) that is communicatively coupled to various components thereof. The controller is configured to control operation of various elements of system 101. For example, the controller is configured to control: delivery of a water sample to cuvette 30 using the inlet valve 64; delivery of reagents (e.g., buffer, indicator, etc.) to cuvette 30 using pump assembly 200; testing of the sample solution with colorimeter 100; etc.

As best shown in FIG. 1B, system 101 further includes first and second reagent tubes 250a, 250b. One end of each of the reagent tubes 250a, 250b can extend into reagent containers 40a and 40b, e.g., through lids 42a, 42b thereof.

Another end of the reagent tubes 250a, 250b is coupled to a nozzle 102, which extends into cuvette 30. Air vent tubes 44a, 44b extend from lids 42a, 42b. In operation, reagent tubes 250a, 250b are disposed within reagent containers 40a, 40b, respectively. Pump 210 causes reagents to flow from reagent containers 40a, 40b, through reagent tubes 250a, 250b and into cuvette 30, e.g., via nozzle 102. At the same or different time, a water sample is introduced into cuvette 30. The reagents (including an indicator) introduced into cuvette 30 combine with the water sample to form a test sample (also referred to as a sample solution). Colorimeter 100 measures the test sample to determine a concentration of a constituent, e.g., chlorine, within the test sample. For example, colorimeter 100 may determine a concentration or amount of the constituent by comparing the color of the test sample with colors of standard solutions containing that constituent. After testing is complete, the test sample is drained from cuvette 30 via drain valve 70 and drain line 72.

While system 101 has proven quite useful, it is not without limitations. For example, when system 101 is used to detect residual chlorine in water, DPD may be used as an indicator that is provided from reagent container 40b to cuvette 30. While DPD can be used to accurately determine an amount of chlorine within a water sample, its effectiveness can decline over time due to oxidation. This issue is particularly problematic when the DPD indicator is used in an aqueous solution. Due to oxidation of the indicator the reagent container 40b (or the reagent therein) may need to be changed before all the indicator therein is used, resulting in significant waste.

Aspects of the present disclosure relate to stabilized reagent compositions, fluid content monitoring systems using the same, and methods using the same. In embodiments the stabilized reagent compositions (also referred to herein as a stabilized indicator composition) include a solvent, an indicator, and a stabilizer for the indicator.

The solvent may be any suitable solvent for the indicator. Non-limiting examples of solvents that may be used in the stabilized reagent composition include water or any other suitable polar, non-polar, or mixed solvent system, combinations thereof, and the like. Without limitation, in embodiments the solvent preferably is or includes water. In embodiments the solvent includes, consists essentially of, or consists of water.

The indicator includes one or more compounds that are configured to indicate the presence and/or amount of at least one constituent in a fluid sample, e.g., colorimetrically. Any suitable indicator may be used as the indicator described herein, provided it can accurately indicate the amount of at least one constituent in a test sample. One non-limiting example of a suitable indicator that may be used is N, N-diethyl-p-phenylene diamine (DPD), but other indicators may also be used. In embodiments, the indicator preferably includes, consists essentially of, or consists of (DPD). In such instances the indicator may be configured to indicate a residual and/or total amount of chlorine in a fluid sample, as understood in the art. Without limitation, in embodiments the indicator includes, consists essentially of, or consists of DPD.

The stabilizer is generally configured to extend the life of the indicator, e.g., by preventing or limiting its oxidation over time. As used herein, "extend the life" means that the stabilizer acts to increase the shelf life of the indicator at a set temperature to longer than the shelf life of the indicator at that temperature without the stabilizer. With that in mind, the inventors have observed that an indicator composition comprising an aqueous solution of DPD has a shelf life of 30 days at 55° C. or a shelf life of 90 days at 25° C. before it needs to be replaced due to oxidation. The stabilizers described herein, when introduced into a solution comprising a solvent and indicator (e.g., DPD), can increase the shelf life of the indicator at 25° C. in aqueous solution to greater than 30 days at 55° C. and greater than 90 days at 25° C., such as greater than or equal to 180 days at 25° C., greater than or equal to 270 days at 25° C., greater than or equal to 365 days at 25° C., or longer.

The stabilizer may be in the form of or include one or more anti-oxidant compounds. Non-limiting examples of suitable stabilizers that can be used in the stabilized reagent compositions include sulfites (e.g., sodium sulfite, potassium sulfite, thiosulfate, etc., combinations thereof, and the like), sulfates (e.g., sodium sulfate, potassium sulfate, thiosulfate, etc. combinations thereof, and the like), combinations thereof, and the like). Without limitation, in embodiments the stabilizer includes, consists essentially of, or consists of an alkali metal sulfite such as sodium and/or potassium sulfite. Alternatively, in embodiments the stabilizer includes, consists essentially of, or consists of an alkali metal sulfate such as sodium and/or potassium sulfate. And in still further embodiments, the stabilizer includes, consists essentially, or consists of a combination of at least one sulfite (e.g., sodium and/or potassium sulfite) and at least one sulfate (e.g., sodium and/or potassium sulfate). In specific non-limiting embodiments, the stabilizer is or includes a sulfite (e.g., sodium sulfite), the indicator is or includes DPD, and the solvent is or includes water.

The stabilizers described herein are preferably selected such that they can be removed from the stabilized indicator composition by a stabilizer removal system, e.g., prior to use of the indicator to facilitate a colorimetric analysis of a fluid sample. In embodiments, the stabilizer removal system includes an ion exchange resin, which may be included in an ion exchange column or other suitable apparatus. In such instances the ion exchange resin may be configured to remove the stabilizer from the stabilized indicator composition. More specifically, when the stabilized indicator composition passes through the ion exchange resin (e.g., in an ion exchange column or other suitable apparatus), the ion exchange resin may retain the stabilizer while allowing other components (e.g., the solvent and indicator) to pass therethrough. In any case, the stabilizer removal system is configured to remove stabilizer from the stabilized indicator composition to provide a fluid stream (i.e., downstream of the stabilizer removal system) that includes the (then unstabilized) indicator. The fluid stream containing the (unstabilized) indicator can then be used in a colorimetric analysis of a fluid sample (e.g., water). For example, when the indicator is DPD the fluid stream containing DPD and a fluid sample (e.g., water) can be provided to a sample chamber (e.g. a cuvette). The DPD may cause the color (hue) of the fluid sample in the sample chamber to change depending on an amount of one or more constituents (e.g., residual and/or total chlorine) present in the sample. A sample analyzer such as photometer (e.g. a colorimeter) may then be used to determine the color/hue of the sample, and in turn determine an amount of the at least one constituent (e.g., residual and/or free chlorine) in the sample.

The stabilized indicator composition may optionally include a buffer (e.g., in addition to the solvent, indicator, and stabilizer). When used, the buffer may be configured to stabilize the pH of the indicator composition within a desired pH range. Any suitable buffers may be used for this purpose. Non-limiting examples of suitable buffers that may be used include citrate, phosphate, and borate buffer systems, such as those used in chlorine monitoring systems. Without limitation, in embodiments the buffer preferably includes, consists essentially of, or consists of a citrate salt, a phosphate salt, or a combination thereof. In specific non-limiting embodiments, the solvent is or includes water, the indicator is or includes DPD, the stabilizer is or includes a sulfite or sulfate (e.g., sodium sulfite), and the buffer is of includes a citrate salt and a phosphate salt. For example, in specific non limiting embodiments the stabilized indicator compositions include from greater than 0 to about 6 weight % of p-toluene sulfonic acid, greater than 0 to about 3 weight % DPD, greater than 0 to about 1% sulfite salt, greater than 0 to about 93 weight % water, and a buffer, wherein the buffer includes greater than 0 to about 6 weight % ethylene diamine tetraacetic acid (EDTA), greater than 0 to about 62 weight % of a citrate salt, greater than 0 to about 37 weight % of a phosphate salt, and greater than 0 to about 26 weight % of potassium iodide.

The stabilized indicator compositions may optionally include additional species. For example, the stabilized indicator compositions may further include a catalyst for the indicator, such as but not limited to sodium nitroprusside. When used, the catalyst may degrade over time due to oxidation. In such instances, the stabilizer for the indicator may also act as a stabilizer for the catalyst, preventing its oxidation and extending its useable life. Without limitation in embodiments the stabilized indicator compositions include sodium nitroprusside as a catalyst, and the stabilizer (e.g., a sulfite, sulfate, etc. as noted above) can stabilize both the catalyst and the indicator, e.g., by limiting or preventing their oxidation.

Another aspect of the present disclosure relates to fluid content monitoring systems that utilize a stabilized indicator composition. In that regard reference is made to FIGS. 2 and 3, which depict non-limiting examples of fluid content monitoring systems consistent with the present disclosure. As shown, fluid content monitoring systems 201, 301 (also referred to herein as system 201 or system 301) includes a reagent store 303, a stabilizer removal system 309, a pump assembly 313, a sample analyzer 315, and a controller 350. The pump assembly 313 is fluidly coupled to the reagent store 303 and the sample analyzer 315, and optionally to sample source 302. The stabilizer removal system 309 is fluidly coupled to the reagent store 303 and the sample analyzer 315.

Figure 2:
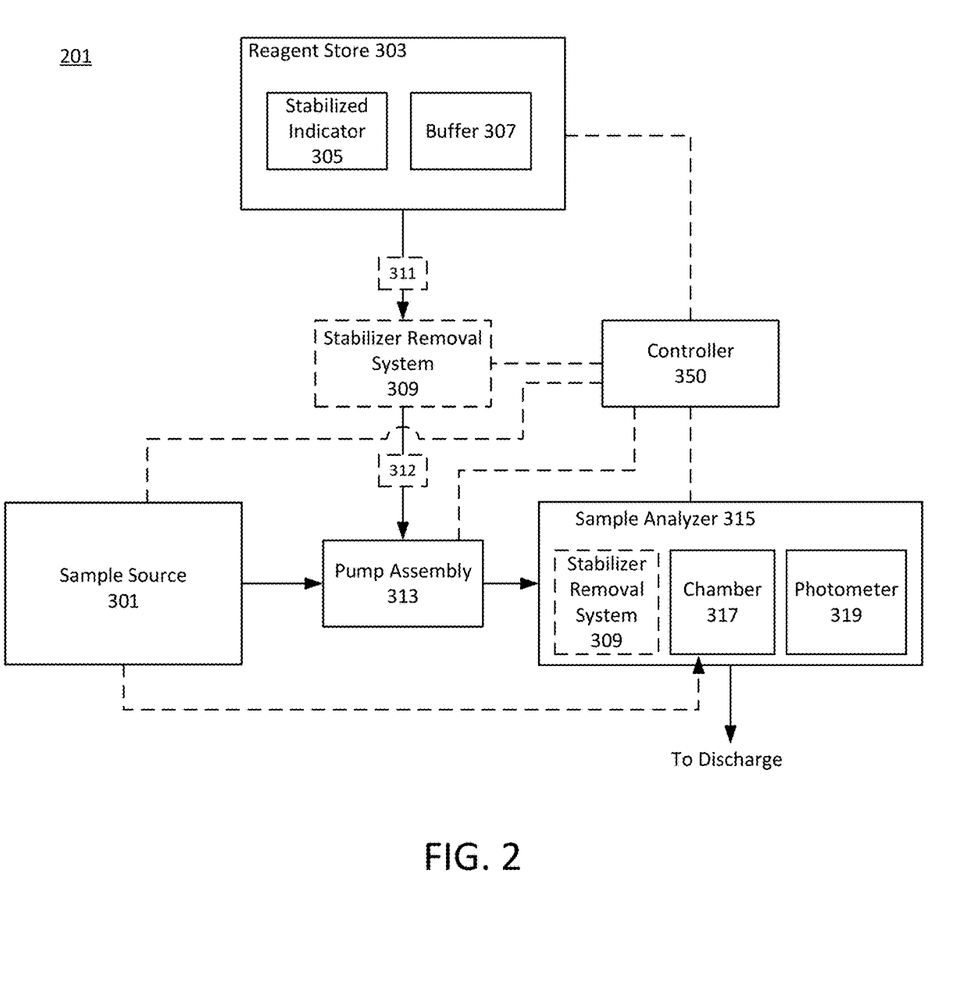
FIG. 2 is a block diagram of one example of a fluid content monitoring system consistent with the present disclosure.
Figure 3:
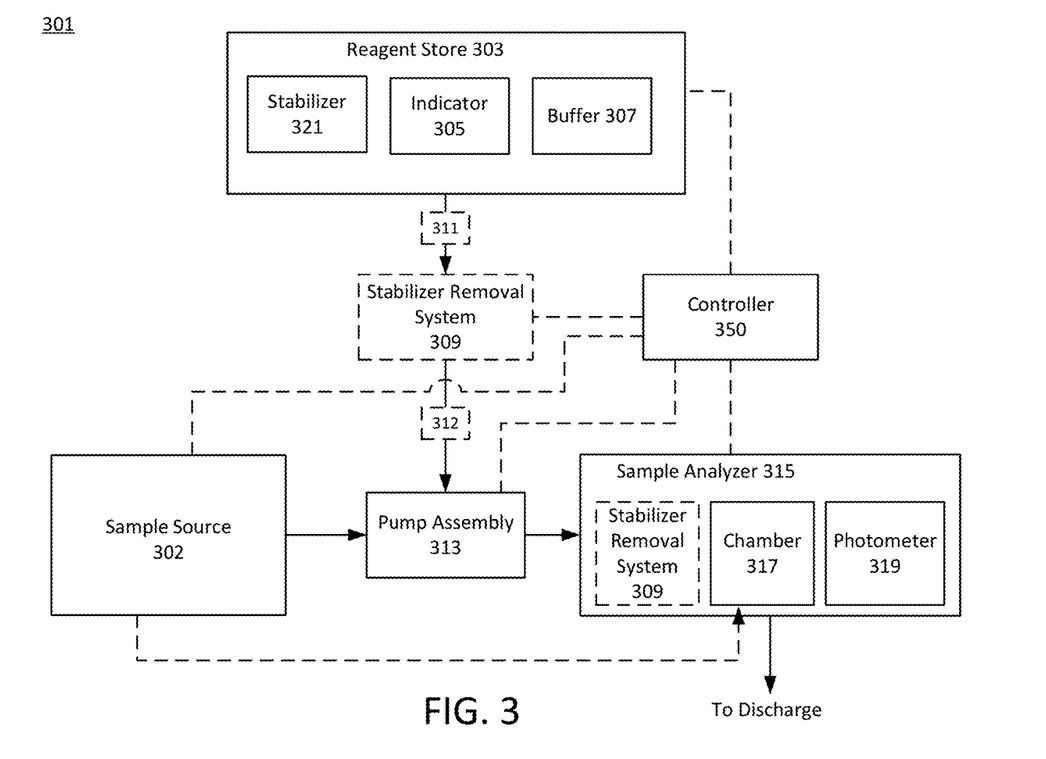
FIG. 3 is a block diagram of another example of a fluid content monitoring system consistent with the present disclosure.

Sample source 302 is generally a source of a liquid that is to be analyzed by sample analyzer 315. Any suitable source of liquid may be used as sample source 302. In embodiments, sample source 302 is a water source, such as a municipal, wastewater, or industrial water supply. Alternatively, sample source 302 may be a container that contains a liquid (e.g., water) to be tested. Without limitation, in embodiments sample source 302 is a municipal, wastewater, or industrial water supply, and pump assembly 313 is plumbed into the sample source 302. In such instances, systems 201, 301 may be understood to be configured as an on-line fluid content monitoring system, as understood in the art. Without limitation, the fluid content monitoring systems described herein are on-line systems that are configured to draw samples from sample source 302 on a continuous, periodic, or intermittent basis.

Reagent store 303 is generally configured to store components of and/or to provide a stabilized indicator composition, e.g., a solvent, stabilizer, indicator, and optional buffer. In embodiments and as shown in FIG. 2, reagent store 303 may include a first container or reservoir 305 (e.g., a first reagent bottle) that includes a stabilized indicator (e.g., a combination of indicator, solvent, and stabilizer), and a second container or reservoir 307 (e.g., a second reagent bottle) that includes a buffer. In embodiments the reagent store 303 may be configured to combine the stabilized indicator, a solvent, and buffer to form a buffered stabilized indicator. For example, reagent store 303 may be configured to provide the stabilized indicator, solvent, and buffer to a mixing valve or other apparatus (not shown), which combines the stabilized indicator, solvent, and buffer to form a buffered stabilized indicator. Alternatively, reagent store 303 may include separate containers and/or reservoirs for storage of the stabilizer, indicator (in a solvent), and buffer. That concept is shown in FIG. 3, which depicts a fluid content monitoring system 301 that includes a reagent store 303 with a first container/reservoir 305 for storing an indicator (e.g., in water or other solvent), a second container/reservoir 307 for storing a buffer, and a third container/reservoir 321 for storing a stabilizer for the indicator. In such instances, reagent store 303 or other elements of system 301 may be configured to combine the stabilizer, indicator (with solvent), and optionally a buffer and/or a catalyst (e.g., with a mixing valve or other apparatus) to form a stabilized indicator composition consistent with the present disclosure, e.g., on an as-needed basis such as when the first container/reservoir 305 is replaced or refilled with unstabilized indicator. And in still further embodiments, reagent store 303 may include a single container or reservoir that includes as stabilizer indicator composition that includes a stabilizer, indicator, solvent, and optionally a buffer and/or a catalyst e.g., as a pre-mixed solution.

Put differently, reagent store 303 is configured to store and provide a stabilized indicator composition that includes at least a solvent, stabilizer, and indicator, and which optionally further includes a buffer and/or other components such as a catalyst. The details of the stabilized indicator composition are the same as described above, and so are not reiterated. In embodiments the indicator in the stabilized indicator composition includes, consists essentially of, or consists of an aqueous solution of DPD and one or more sulfite or sulfate stabilizers, such as an alkali metal (e.g., sodium) sulfite and/or sulfate. For example, the stabilized indicator composition may include, consist essentially of, or consist of a solution of water, DPD, and sulfite and/or sulfate stabilizer (e.g., alkali metal sulfite). In such instances at least one constituent in the sample may include residual or total chlorine in the sample.

Pump assembly 313 is generally configured to cause the stabilized indicator composition to flow through stabilizer removal system 309. In some instances, and as shown in FIGS. 2 and 3, pump assembly 313 may also be configured to cause a fluid (e.g., water) from sample source 302 to flow into sample analyzer 315 or, more specifically, into a chamber 317 within sample analyzer 315 (e.g., a cuvette). In that regard, pump assembly 313 may include one or more pumps that is/are configured to cause the stabilized indicator composition and a fluid from sample source 302 to flow at a desired flow rate, e.g., as may be determined by controller 350. Alternatively or additionally, systems 201, 301 may be configured such that pump assembly 313 causes the indicator composition to flow into sample analyzer 315, whereas a fluid from sample source 302 is provided to sample analyzer 315 in another manner. For example, in embodiments the fluid from sample source 302 may be provided to sample analyzer 315 while bypassing pump assembly 313. Indeed, and as shown with a broken line in FIGS. 2 and 3, a sample from sample source 302 may be provided directly to a chamber 317 (e.g., a cuvette) within sample analyzer 315 without passing through pump assembly 313.

In general, stabilizer removal system 309 is configured to remove the stabilizer from the stabilized indicator composition prior to the combination of the stabilizer with the fluid from sample source 302. Removal of the stabilizer from the stabilized indicator composition produces a fluid stream that includes the solvent and the (un-stabilized) indicator. Preferably, all the stabilizer is removed from the stabilized indicator composition by stabilizer removal system 309. In embodiments, however, stabilizer removal system 309 may be configured to removal substantially all the stabilizer from the stabilized indicator composition. In that context removal of substantially all the stabilizer from the stabilized indicator composition means that while the stabilizer removal system 309 removes most of the stabilizer from the stabilized indicator composition, but a residual amount of stabilizer may remain present in the fluid flow downstream of the stabilizer removal system 309. In such instances, the amount of residual stabilizer in the fluid flow downstream of the stabilizer removal system may be less than an amount that will affect the ability of the indicator to accurately (i.e., within +/−5%) indicate an amount of a constituent (e.g., chlorine) within a sample from sample source.

Stabilizer removal system 309 may be located at any suitable position within systems 201, 301. As shown in FIGS. 2 and 3, stabilizer removal system 309 is preferably located upstream of pump assembly 313. However, stabilizer removal system 309 may be positioned at another suitable location, such as downstream of pump assembly 313 (e.g., between pump assembly 313 and sample analyzer 315, or even within sample analyzer 315 as shown in FIGS. 2 and 3. In still further embodiments, multiple (e.g., 2, 3, 4, 5, 6 or more) stabilizer removal systems 309 may be used. In such instances, the stabilizer removal systems 309 may be arranged in a fluid series such that each of those systems progressively remove stabilizer from the stabilized indicator composition. In any case, the stabilizer removal system 309 is generally configured to remove stabilizer from the stabilized indicator composition before (or after) the indicator is mixed with the fluid from sample source 302. Without limitation, in embodiments the stabilizer removal system is arranged within systems 201, 301 to such that all or substantially of the stabilizer is removed from the stabilized indicator composition before the indicator is mixed with the fluid from sample source 302.

Stabilizer removal system 309 may be any suitable type of stabilizer removal system, provided it can adequately remove stabilizer from the stabilized indicator composition. In embodiments, stabilizer removal system 309 is or includes an ion exchange resin that is configured to retain the stabilizer while allowing other components of the stabilized indicator composition to pass therethrough. For example, stabilizer removal system 309 may include or be in the form of an ion exchange column that includes an ion exchange resin, an inlet and an outlet. The pump assembly 313 may be configured to cause the stabilized indicator composition to flow into the inlet of the ion exchange column and through the ion exchange resin. As the stabilized indicator composition flows through the ion exchange resin, the resin retains the stabilizer (via ion exchange) while allowing the indicator and other components (e.g., the solvent) to flow out of the outlet of the ion exchange column. As a result, a fluid stream including the (un-stabilized) indicator is provided downstream of the ion exchange column/resin. Without limitation, the fluid stream downstream of the ion exchange resin/column preferably contains no stabilizer, or contains a residual amount of stabilizer as described above.

Any suitable ion exchange resin may be used in stabilizer removal system 309 (e.e., cationic, anionic, and/or ampho-teric ion exchange resins), depending on the type of stabilizer used in the stabilized indicator composition. Without limitation, the stabilizer is preferably a sulfite or sulfate stabilizer (e.g., an alkali metal sulfite and/or sulfate), and stabilizer removal system 309 preferably includes, consists essentially of, or consists of a anionic exchange resin, e.g., in an ion exchange column or other suitable structure. One non-limiting example of an anionic ion exchange resin that can be used is the Purolite® A300 anionic exchange resin, but other anionic exchange resins (e.g., Purolite A301, A302, etc.) may also be used. In some embodiments the stabilizer is or includes a sulfite (e.g., sodium sulfite), the indicator is or includes DPD, and the stabilizer removal system 309 includes an anionic exchange resin that is configured to remove the sulfite stabilizer from the stabilized indicator composition, resulting in the production of a fluid stream that includes (un-stabilized) DPD, solvent (e.g., water), and optionally a buffer and/or other components such as a catalyst.

Systems 201, 301 may optionally include one or more check valves. For example, and as shown in FIGS. 2 and 3, systems 201, 301 may optionally include a check valve 311 upstream of stabilizer removal system 309. The check valve 311 may be configured to prevent backflow of fluid (particularly fluid containing un-stabilized indicator such as unstabilized DPD) from stabilizer removal system 309 into reagent store 303. While FIGS. 2 and 3 show a single check valve 311, multiple check valves 311 may be used and may be positioned at any suitable location within systems 201, 301.

Systems 201 and 301 may also optionally include one or more filters 312. In embodiments and as shown in FIGS. 2 and 3, systems 201, 301 may optionally include a filter 312 downstream of stabilizer removal system 309. The filter 312 may be configured to prevent migration of components of the stabilizer removal system 309 (e.g. ion exchange resin used therein) into downstream components of system 201, 301, such as pump assembly 313 and/or sample analyzer. Non limiting examples of suitable filters that may be used or in filter 312 include cotton filters, paper filters, nylon filters combinations thereof, and the like.

Pump assembly 313 is further configured to cause the fluid stream containing the (un-stabilized) indicator) and a fluid (e.g., water) from sample source 302 to be conveyed to a chamber 317 in sample analyzer 315 (e.g., a cuvette) to form a test sample including the (un-stabilized) indicator and the sample. The sample analyzer 315 is configured to analyze the test sample to determine an amount of at least one constituent in the sample, e.g., chlorine. In embodiments, the sample analyzer 315 is or includes a photometer 319 (e.g., a colorimeter) and the sample analyzer is configured to determine an amount of at least one constituent in the test sample via colorimetric analysis as understood in the art. For example, when the indicator is DPD or another chlorine indicator), sample analyzer 315 may include a photometer 319 that is configured to determine an amount of total or residual chlorine in the test sample colorimetrically, as understood in the art.

As noted above, systems 201, 301 further include a controller 350. In general, controller 350 is configured to control the operation of various components of systems 201, 301, e.g., during the performance of a measurement on a sample. In embodiments controller 350 may include a processor and a memory that includes computer readable instructions which when executed by the processor cause the controller to perform sample testing operations consistent with the present disclosure. In embodiments the sample testing operations may include causing reagent store 303 to produce a stabilized indicator composition. Such operations may further include causing pump assembly 313 to cause a stabilized indicator composition to flow through stabilizer removal system 309 (e.g. at a desired flow rate), thereby producing a fluid flow that includes an (un-stabilized) indicator. The sample testing operations may further include causing the formation of a test sample, e.g., by causing the fluid flow containing the (unstabilized) indicator and a fluid from sample source 302 (e.g., water) to be combined, e.g., within chamber 317 of sample analyzer 315. The sample testing operations may also include causing sample analyzer 315 (or, more specifically, photometer 319) to determine an amount of at least one constituent (e.g., chlorine) within the test sample, e.g., via colorimetric analysis or in another manner.

Figure 4:
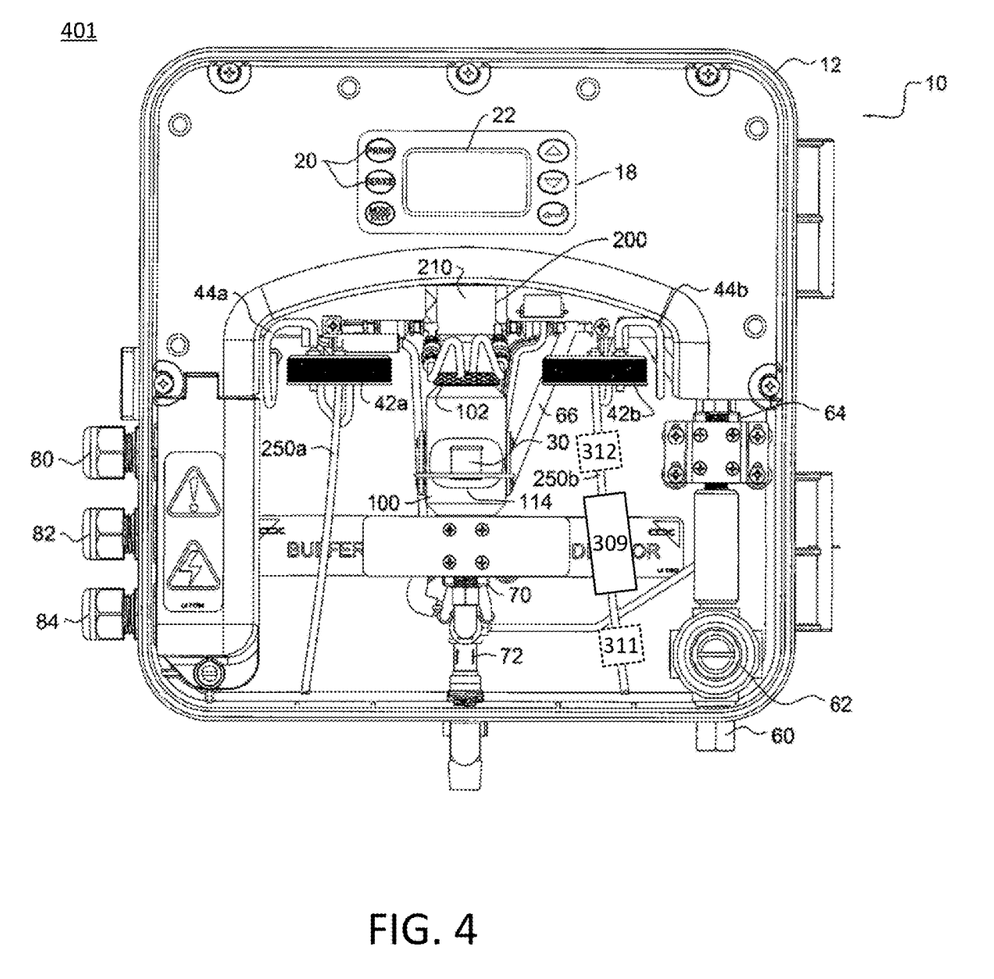
FIG. 4 depicts another example of a fluid content monitoring system consistent with the present disclosure.

FIG. 4 illustrates another example of a fluid content monitoring system consistent with the present disclosure. System 401 includes many of the same components as system 101 described above in connection with FIGS. 1A and 1B and further described in U.S. Pat. No. 7,794,660, which is again incorporated herein by reference. Accordingly, such components and their function are not described again in the interest of brevity. In addition to the components described in connection with system 101, system 401 includes a stabilizer removal system 309 that is fluidly coupled to reagent tube 250b. As described above, reagent tube 250b is configured to extend into a reagent container 40b (not shown in FIG. 4 but shown in FIG. 1A). With that in mind and unlike system 101, reagent container 40b is configured to contain a stabilized indicator composition consistent with the present disclosure. For example, reagent container 40b may contain an aqueous solution of an indicator (e.g., DPD) and a stabilizer for the indicator (e.g., a sulfite or sulfate, such as an alkali metal sulfite and/or sulfate such as sodium sulfite/sulfate). In embodiments, stabilizer removal system 309 is or includes an ion exchange resin, such as an ion exchange column including an ion exchange resin. Without limitation, stabilizer removal system 309 is an ion exchange column that includes an inlet and an outlet, and an anionic, cationic, or amphoteric ion exchange resin therebetween. In embodiments the stabilized indicator composition is an aqueous solution containing DPD and a stabilizer (e.g., an alkali metal sulfite or sulfate), and stabilizer removal system 309 includes an anionic ion exchange resin that is configured to remove the stabilizer from the stabilized indicator composition while allowing the indicator and water to pass therethrough.

Like systems 201, 301, system 401 may include an optional check valve 311. For example and as shown in FIG. 4, system 401 may include a check valve 311 that is fluidly coupled to reagent tube 250b, e.g., upstream of an inlet to stabilizer removal system 309. In such instances check valve 311 may function to prevent backflow of unstabilized indicator from stabilizer removal system into reagent container 40b and, thus, prevent contamination of the stabilized indicator composition therein. Similarly, system 401 may include an optional filter 312. For example, and as shown in FIG. 4, system 401 may include a filter 312 downstream of stabilizer removal system 309. When stabilizer removal system is or includes an ion exchange resin, filter 312 may be configured to prevent the ion exchange resin from flowing to downstream components of system 401, e.g., by filtering any such resin that maybe present in the fluid flow downstream of stabilizer removal system 309.

Operationally, system 401 functions to detect constituent contents in samples in much the same manner as described above in connection with system 101, except that it utilizes a stabilized indicator composition and a stabilizer removal assembly as described above in connection with systems 201, 301. That is, reagent tube 250b may be fluidly coupled to a reagent container 40b that includes a stabilized indicator composition, such as an aqueous solution of DPD and sulfite and/or sulfate stabilizer. Reagent tube 250a may be fluidly coupled to a reagent container 40a containing a buffer. To analyze a fluid (e.g., water) sample, a fluid (e.g., water) is provided from a sample source into a cuvette 30. Pump 210 then causes reagents to flow through reagent tubes 250a, 250b. More particularly, pump 210 causes stabilized indicator composition to flow through reagent tube 250b and through stabilizer removal system 309, e.g., into the inlet of an ion exchange resin. Stabilizer removal system 309 removes all or substantially all the stabilizer (e.g., sulfite or sulfate) from the stabilized indicator composition as described above, resulting in a fluid flow that contains an un stabilized indicator (e.g., un stabilized DPD). At the same time, pump 210 causes buffer to flow out of reagent container 40a via reagent tube 250a. The fluid flow containing the un stabilized indicator flows out of the outlet of stabilizer removal system 309 is combined with the buffer to form a buffered stabilized indicator composition, which is introduced into cuvette 30. The buffered stabilized indicator composition combines with the fluid from the sample source in cuvette 30 to form a test sample. The indicator changes the color of the test sample based on the content of at least one constituent (e.g., chlorine) in the fluid from the sample source. Colorimeter 100 measures the test sample to determine a concentration of a constituent, e.g., chlorine, within the sample. For example, colorimeter 100 may determine a concentration or amount of the constituent by colorimetric analysis or in another manner. After the measurement is complete the test sample is drained from cuvette 30 via drain valve 70 and drain line 72.

In embodiments and as discussed above, the stabilizer removal systems described herein may be in the form of an ion exchange column that includes an ion exchange resin. While such a configuration is useful the stabilizer removal systems described herein are not limited thereto and may be configured differently. For example, in embodiments stabilizer removal system 309 may be integrated into one or more reagent containers (e.g., a reagent bottle) which can be used to store a stabilized indicator composition. In such instances the reagent container may be configured such that the stabilized indicator composition is drawn through the stabilizer removal system as it is withdrawn from the reagent container. For example, the stabilizer removal system may include a bed or other structure containing ion exchange resin, which may be located within a wall or lid of the reagent container, and which is fluidly coupled to a fluid outlet from the reagent container. As a result, stabilized indicator composition will be drawn through the ion exchange resin as it is drawn from the reagent container, resulting in a fluid flow downstream of the reagent container that include an un stabilized indicator.

Figure 5:
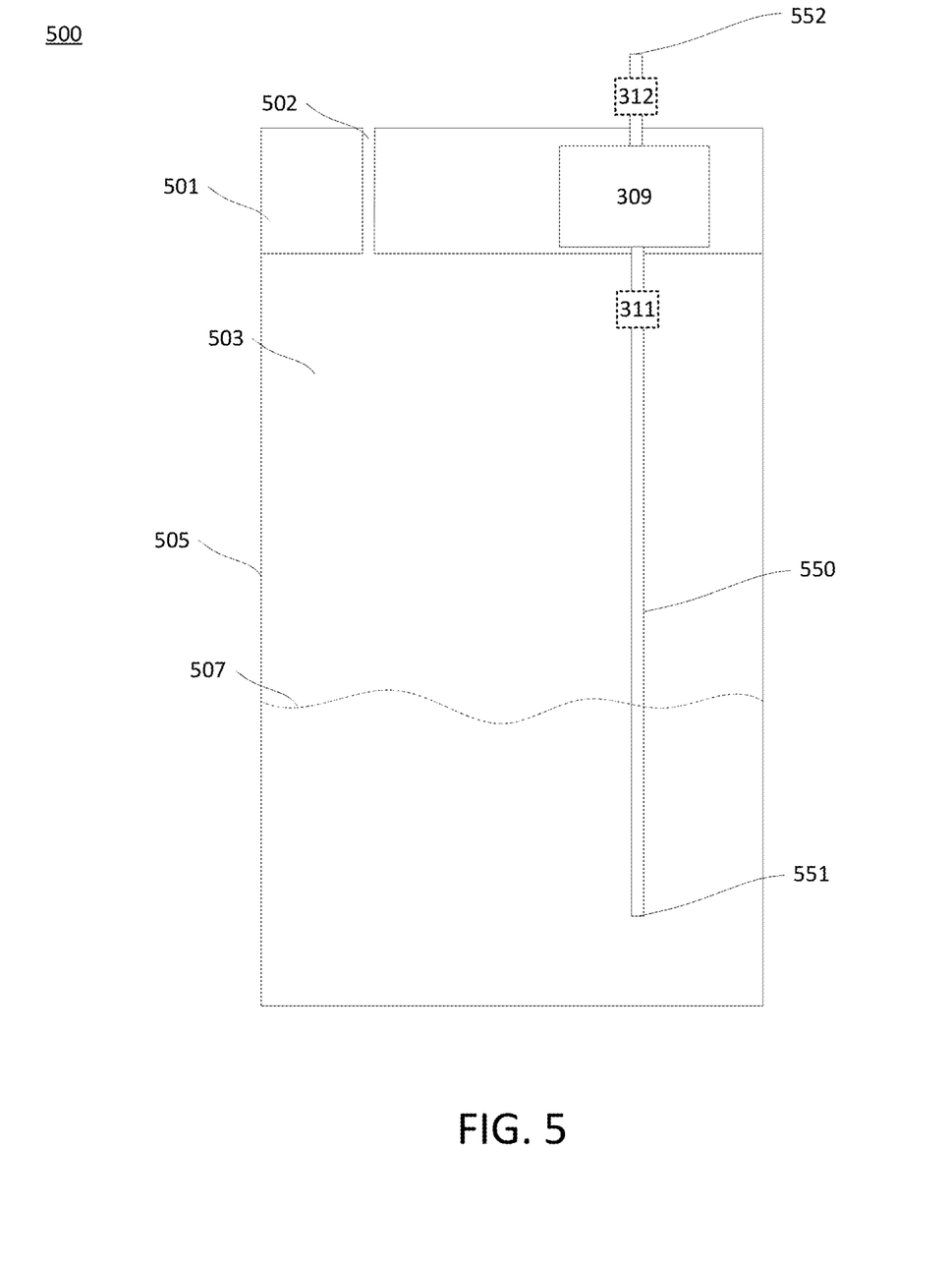
FIG. 5 depicts one example of a reagent bottle including a stabilizer removal system consistent with the present disclosure.

FIG. 5 depicts one example of such a reagent container. As shown, container 500 includes a lid 501 and a body 503. The body includes at least one wall 505 (e.g., 1, 3, 4, 5, 6, 7, etc.), and may have any suitable cross sectional shape (e.g., circular, ellipsoidal, triangular, quadrilateral, etc.). Lid 501 may be coupled to body 503 in any suitable manner, such as via a threaded fitting, a hinge, combinations thereof, or the like. An air gap 502 may be formed in lid 501 to facilitate the withdrawal of stabilized indicator composition from container 500. A tube 550 (or other fluid passageway) with a first end 551 and a second end 552 may extend through lid 501 and into a cavity within body 503, as shown. When container 500 includes stabilized indicator composition, the tube 550 maybe of a length such that the first end 551 extends below a level 507 of the stabilized indicator composition.

Container 500 may further include a stabilizer removal system 309, the details of which are generally the same as described above and so are not reiterated in the interest of brevity. Unlike previous embodiments, however, stabilizer removal system 309 in this embodiment is located within or along an interior surface of lid 501. More specifically, stabilizer removal system may include an ion exchange resin that is located within or along a surface of lid 501, and which is in fluid communication with tube 550. As a result, as stabilized indicator composition is drawn up tube 550 it may flow through stabilizer removal system 309. As described above, the stabilizer removal system 309 removes stabilizer from the stabilize indicator composition to produce a downstream fluid flow that includes (un stabilized) indicator, but does not (or does not substantially) include the stabilizer.

Although the illustrated configuration of container 500 is useful, the reagent containers described herein may be configured differently. For example, in embodiments the reagent container herein include a stabilizer removal system 309 that is disposed within a fluid passageway in at least one wall (e.g., a sidewall, bottom, or top) of container 500. Like container 500, the stabilizer removal system 309 in such embodiments is positioned such the stabilized indicator composition is drawn through the stabilizer removal system 309 as the stabilized indicator composition is drawn from the container.

Further aspects of the present disclosure relate to methods of detecting at least one constituent of a fluid. In that regard reference is made to FIG. 6, which depicts one example of a method 600 of detecting at least one constituent of a fluid consistent with the present disclosure. Method 600 begins at block 601. The method may then proceed to block 603, pursuant to which a stabilized indicator composition may be provided. As discussed above, the stabilized indicator composition may be provided as a pre-mixed aqueous solution of an indicator (e.g., DPD), a stabilizer (e.g., a sulfite, sulfate, or the like) for the indicator, and a solvent. Alternatively, the stabilized indicator composition may be provided by mixing a stabilizer, indicator, and solvent. Following the operations of block 603 the method may proceed to block 605, pursuant to which the stabilizer may be removed from the stabilized indicator composition, e.g., with a stabilizer removal system as described above. The result of block 605 may be the production of a fluid flow that contains un stabilized indicator and solvent, but does not (or does not substantially) contain the stabilizer. The method may then proceed to block 607, pursuant to which the fluid flow containing the (un stabilized) indicator and a fluid sample are mixed to form a test sample as described above.

Figure 6:
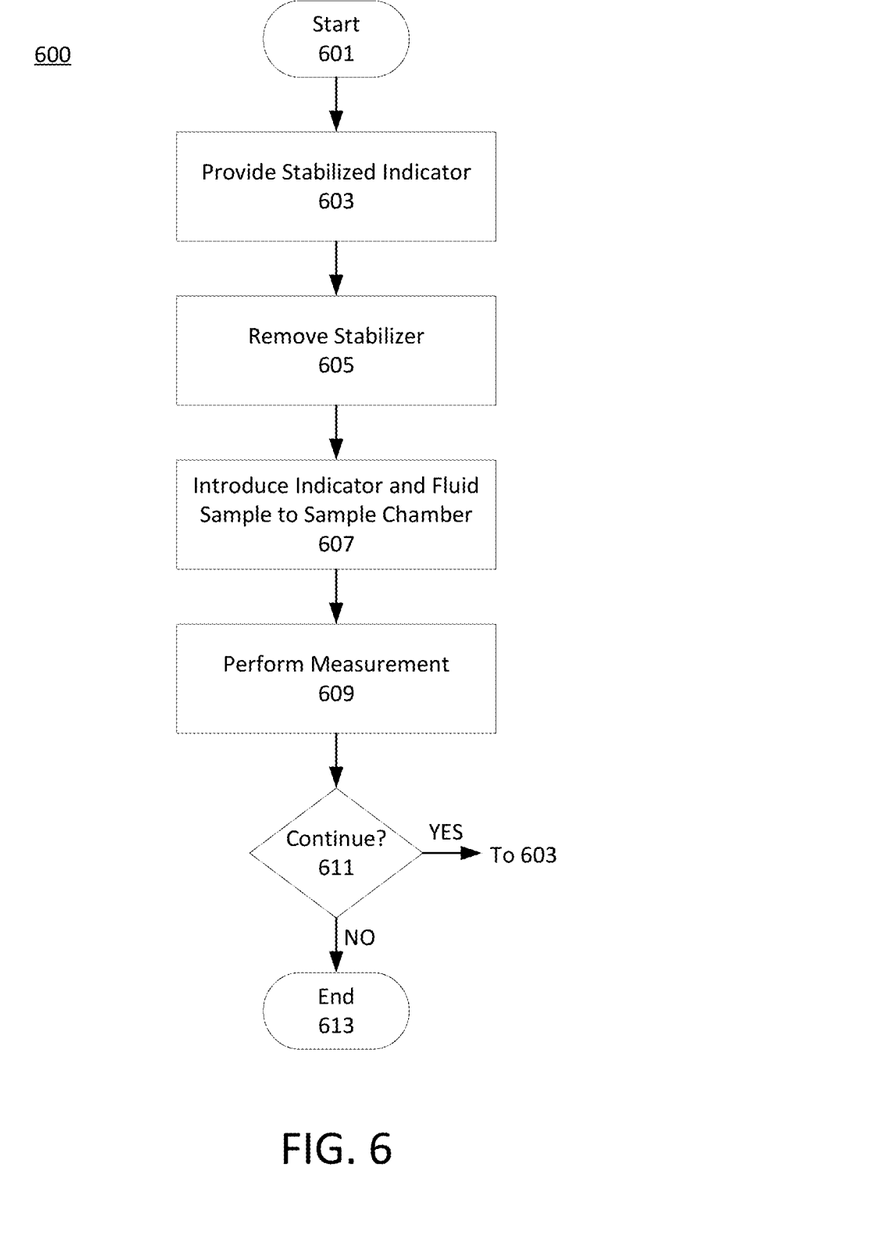
FIG. 6 is a flow diagram of example operations of one example of a fluid content monitoring method consistent with the present disclosure.

The method may then proceed to block 609, pursuant to which a measurement may be performed on the test sample to determine an amount of at least one constituent of the test sample. The measurement may be performed via colorimetric analysis as described above or in any other suitable manner. The method may then proceed to block 611, pursuant to which a determination may be made as to whether the method is to continue. The outcome of block 611 may be conditioned on whether additional measurements are to be taken by the system. If so, the method may loop back to block 603. But if not, the method may proceed to block 613 and end.

As may be appreciated from the foregoing, use of the stabilizer in the stabilized indicator composition can improve the shelf life of the indicator, e.g., by limiting or even preventing its oxidation over time. As a result, the stabilized indicator composition can be stored for a prolonged period without (or without substantially) affecting the ability of the indicator to accurately indicate an amount of a constituent in a fluid sample. For example, when the indicator is DPD, the stabilized indicator composition may be stored for greater than 90 days (e.g., 180, 270, 365, or even more days) without (or without substantially) affecting the ability of the DPD to accurately detect an amount of chlorine or other substituent within a water sample. The stabilizer can also be removed from the stabilized indicator composition via ion exchange or another suitable technique, rendering a fluid stream that includes the (un-stabilized) indicator and which is ready for immediate use in detecting an amount of at least one constituent in a sample under consideration.

As used herein, the term "about" when used in connection with a value or a range, means +/−5% of the indicated value or the indicated endpoints of the range.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A fluid content monitoring system, comprising:
   a reagent store comprising a stabilized indicator composition, the stabilized indicator composition comprising a solvent, a stabilizer, and an indicator, the indicator configured to indicate an amount of one or more constituents in a fluid sample;
   a pump assembly fluidly coupled to a sample source and the reagent store;
   a sample analyzer fluidly coupled to the pump assembly; and
   a stabilizer removal system fluidly coupled to the reagent store and the sample analyzer; wherein:
   the pump assembly is configured to cause said stabilized indicator composition to flow through said stabilizer removal system, thereby causing the stabilizer removal system to remove the stabilizer from the stabilized indicator composition and produce a fluid stream comprising said solvent and said indicator;

said pump assembly is further configured to convey said fluid stream and a fluid from said sample source to a chamber in said sample analyzer to form a test sample; and said sample analyzer is configured to analyze the test sample to determine an amount of at least one constituent in said test sample;

wherein:

said reagent store comprises a reagent container; and at least a portion of said stabilizer removal system is disposed within said reagent container.

2. The fluid content monitoring system of claim 1, wherein said indicator comprises N, N-diethyl-p-phenylene diamine (DPD).

3. The fluid content monitoring system of claim 2, wherein said stabilizer comprises a sulfite.

4. The fluid content monitoring system of claim 2, wherein said stabilizer removal system comprises an ion exchange column comprising an ion exchange resin.

5. The fluid content monitoring system of claim 2, wherein said fluid from said sample source comprises water, said sample analyzer comprises a photometer, and said at least on constituent comprises chlorine.

6. The fluid content monitoring system of claim 1, wherein said stabilizer comprises a sulfite, a sulfate, or a combination thereof.

7. The fluid content monitoring system of claim 1, wherein said stabilizer removal system comprises an ion exchange resin and at least a portion of said ion exchange resin is disposed within said reagent container.

8. The fluid content monitoring system of claim 7, wherein:

said reagent container comprises a container and a lid; and at least a portion of said ion exchange resin is disposed within said lid.

9. The fluid content monitoring system of claim 1, wherein said stabilizer removal system comprises an ion exchange column comprising an ion exchange resin.

10. The fluid content monitoring system of claim 9, further comprising a check valve upstream of the ion exchange resin and a filter downstream of the ion exchange resin.

11. The fluid content monitoring system of claim 1, wherein said fluid from said sample source comprises water, said sample analyzer comprises a photometer, and said at least one constituent comprise chlorine.

12. The fluid content monitoring system of claim 1, wherein said sample source is a municipal water supply, an industrial water supply, a waste water supply, or a combination thereof, and said fluid from said sample source comprises water.

13. A fluid content monitoring system, comprising:

a reagent store comprising a stabilized indicator composition, the stabilized indicator composition comprising a solvent, a stabilizer, and an indicator, the indicator configured to indicate an amount of one or more constituents in a fluid sample;

a pump assembly fluidly coupled to a sample source and the reagent store;

a sample analyzer fluidly coupled to the pump assembly; and a stabilizer removal system fluidly coupled to the reagent store and the sample analyzer, the stabilizer removal system comprising an ion exchange column comprising an ion exchange resin; wherein:

the pump assembly is configured to cause said stabilized indicator composition to flow through said stabilizer removal system, thereby causing the stabilizer removal system to remove the stabilizer from the stabilized indicator composition and produce a fluid stream comprising said solvent and said indicator;

said pump assembly is further configured to convey said fluid stream and a fluid from said sample source to a chamber in said sample analyzer to form a test sample;

said sample analyzer is configured to analyze the test sample to determine an amount of at least one constituent in said test sample; and a check valve upstream of the ion exchange resin and a filter downstream of the ion exchange resin.

\* \* \* \* \*